(12) United States Patent
Jow et al.

(10) Patent No.: US 11,143,885 B2
(45) Date of Patent: Oct. 12, 2021

(54) SMART CONTACT LENS WITH ANTENNA AND SENSOR

(71) Applicant: Verily Life Sciences LLC, Mountain View, CA (US)

(72) Inventors: Uei-Ming Jow, Mountain View, CA (US); Christian Gutierrez, San Francisco, CA (US); Shungneng Lee, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 289 days.

(21) Appl. No.: 16/136,030

(22) Filed: Sep. 19, 2018

(65) Prior Publication Data

US 2019/0094570 A1 Mar. 28, 2019

Related U.S. Application Data

(60) Provisional application No. 62/562,655, filed on Sep. 25, 2017.

(51) Int. Cl.
*G02C 7/02* (2006.01)
*A61B 3/113* (2006.01)
(Continued)

(52) U.S. Cl.
CPC .............. *G02C 7/022* (2013.01); *A61B 3/113* (2013.01); *A61B 5/002* (2013.01); *A61B 5/686* (2013.01);
(Continued)

(58) Field of Classification Search
CPC .......... G02C 7/022; G02C 7/04; G02C 7/083; G02C 11/10; A61B 3/113; A61B 5/002;
(Continued)

(56) References Cited

U.S. PATENT DOCUMENTS 4,850,689 A * 7/1989 Martin ................... G02C 7/048
351/159.74
8,857,983 B2 10/2014 Pugh et al.
(Continued)

FOREIGN PATENT DOCUMENTS

| KR | 191581814 B1 | 1/2016 |
| WO | 2011/083105 A1 | 7/2011 |
| WO | 2015/157855 A1 | 10/2015 |

OTHER PUBLICATIONS

International Search Report and Written Opinion from the International Searching Authority dated Jan. 16, 2019, for International Application No. PCT/US2018/052064, filed Sep. 20, 2018, 14 pages.

(Continued)

*Primary Examiner* — Travis S Fissel
(74) *Attorney, Agent, or Firm* — Christensen O'Connor Johnson Kindness PLLC

(57) ABSTRACT

An ophthalmic device includes an enclosure, an antenna, a sensor system, and a first conductive trace. The ophthalmic device is configured to mount on or in an eye of a user and includes a central region surrounded by a peripheral region. The antenna is disposed within the peripheral region between an outer edge of the ophthalmic device and the central region. The sensor system includes a sensor trace disposed within the peripheral region between the antenna and the central region. The first conductive trace is at least partially disposed between at least one of the antenna and the sensor trace or the central region and the sensor trace.

21 Claims, 6 Drawing Sheets

(51) Int. Cl.
*G02C 7/04* (2006.01)
*G02C 7/08* (2006.01)
*A61F 9/00* (2006.01)
*A61B 5/00* (2006.01)
*G02C 11/00* (2006.01)

(52) U.S. Cl.
CPC .......... *A61B 5/6821* (2013.01); *A61B 5/6867* (2013.01); *G02C 7/04* (2013.01); *G02C 7/083* (2013.01); *G02C 11/10* (2013.01); *A61B 2560/0214* (2013.01); *A61B 2560/0219* (2013.01); *A61B 2560/0462* (2013.01); *A61B 2560/0468* (2013.01); *A61B 2562/222* (2013.01); *A61F 9/0017* (2013.01)

(58) Field of Classification Search
CPC ..... A61B 5/686; A61B 5/6867; A61B 5/6821; A61B 2560/0214; A61B 2560/0219; A61B 2560/0462; A61B 2560/0468; A61B 2562/222; A61F 9/0017
USPC ............ 351/159.01–159.03, 159.39, 159.73, 351/159.74, 178
See application file for complete search history.

(56) References Cited

U.S. PATENT DOCUMENTS

| | | | |
|---|---|---|---|
| 9,192,298 | B2 | 11/2015 | Bouwstra et al. |
| 9,259,309 | B2 | 2/2016 | Fehr et al. |
| 2009/0033863 | A1* | 2/2009 | Blum ...................... G02C 7/16 351/159.34 |
| 2012/0245444 | A1 | 9/2012 | Otis et al. |
| 2015/0362754 | A1* | 12/2015 | Etzkorn .................. G02C 7/04 351/159.03 |
| 2016/0091737 | A1 | 3/2016 | Kim et al. |
| 2017/0189169 | A1 | 7/2017 | Haddock et al. |
| 2017/0227792 | A1 | 8/2017 | Starner et al. |
| 2017/0255026 | A1 | 9/2017 | Rakhyani et al. |
| 2018/0246049 | A1 | 8/2018 | Gutierrez |

OTHER PUBLICATIONS

Liao, Yu-Te et al., "A 3-µW CMOS Glucose Sensor for Wireless Contact-Lens Tear Glucose Monitoring", IEEE Journal of Solid-State Circuits, vol. 47, No. 1, Jan. 2012, 10 pages.

* cited by examiner

SMART CONTACT LENS WITH ANTENNA AND SENSOR

CROSS-REFERENCE TO RELATED APPLICATIONS

This application claims the benefit of U.S. Provisional Application No. 62/562,655, filed Sep. 25, 2017, which is hereby incorporated by reference in its entirety.

TECHNICAL FIELD

This disclosure relates generally to the field of wirelessly connected biometric sensors, and in particular but not exclusively, relates to contact lenses.

BACKGROUND INFORMATION

Contact lenses are worn by a large number of people throughout the world, mainly for the purpose of vision correction. However, as lens technology continues to progress, the functionality of contact lenses may extend beyond merely providing static vision correction to other areas. For example, eye-mountable devices (EMD), smart contact lenses, or intraocular lenses, may offer unique opportunities in health monitoring, biometric sensing, dynamic vision correction, and other types of vision augmentation.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
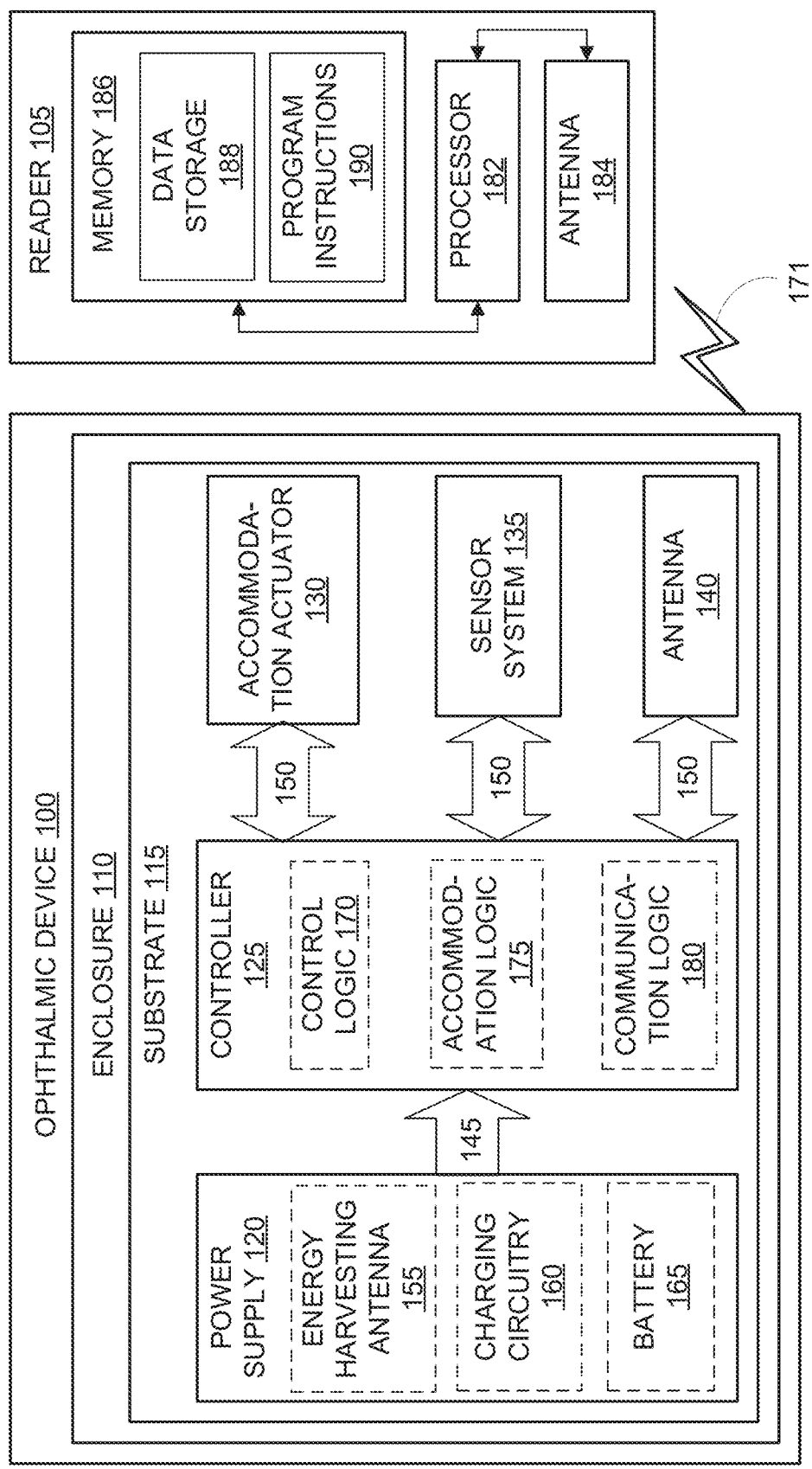
FIG. 1 illustrates a functional block diagram of an ophthalmic device with an antenna and sensor system along with an external reader, in accordance with an embodiment of the disclosure.

Embodiments of ophthalmic devices are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As the functionality of EMDs and smart contact lenses increases, the complexity of the device architecture follows suit. Thus, design engineers must carefully balance the integration of electronics and other components with the physical limitations of an optical device that operates on a human eye. For example, successive generations of eye-mountable devices continue to scale down in size and scale up in functionality, there is expected to be an increased demand for such optical devices to efficiently utilize the limited physical space available. Accordingly, incremental improvement in the utilization of such physical space is expected to significantly impact the usability and functionality of eye-mountable devices.

Designers of ophthalmic devices (e.g. eye-mountable devices, smart contact lenses, and intraocular lenses) have to integrate several electronics and other components within a small area for a user's comfort. Eye-mountable devices, for example, are generally limited to placing nontransparent electronic components at a periphery of the device in order to prevent obstruction of the user's field of view. However, this integration could cause interference or parasitic effects between device components. Interference or parasitic effects may result from unintentional electromagnetic coupling between components, such as capacitive coupling, inductive coupling, and electromagnetic interference.

In one embodiment, an eye-mountable device may include a battery, an antenna for wireless communication or charging of the battery and a sensor system for gaze detection, analyte monitoring, hydration detection, and other functionalities. The sensor system may include sensing components such as capacitors, photodiodes, electrochemical sensors, metal electrodes/traces, and the like. When the sensing components and radiation components (e.g. the antenna) are in close proximity, the gain of the antenna may be degraded by the sensing components due to energy absorption. Such degradation may prevent the formation of a stable wireless link between the eye-mountable device and another device (e.g. an external reader) or diminish the effectiveness of the antenna to inductively charge the battery.

In order to integrate several conductive traces, such as sensor traces, connection traces, and antennas on an individual device, a layout of said components (and others) to reduce unwanted parasitic effects between components is described in the various embodiments of the disclosure.

In some embodiments, the eye-mountable device includes a loop antenna, a sensor, and metal traces. It is noted that in various embodiments, the term loop may correspond to a partial loop such as an arc or open loop that starts at a first position and ends at a second position different from the first position or a complete loop that starts and ends at the same position. In one embodiment, the loop antenna is disposed in an outside portion of the lens proximate to the edge of the eye-mountable device. The sensor is a metal trace that is inside, or otherwise encircled by, the antenna. In some embodiments, the sensor forms an arc or a loop within the eye-mountable device that has a radius less than the radius of the antenna loop. The eye-mountable device may include additional metal traces (e.g. a first conductive trace and a second conductive trace) comprising Au, Ag, Al, Pt, Cu, Ni, Ti, Sn, or a combination thereof. The additional metal traces are disposed adjacent to the sensor on opposite sides of the sensor to cancel, shield, or otherwise reduce electromagnetic interference (e.g. cross-talk, loop effect, capacitive coupling, and/or inductive coupling) that occurs when the sensor absorbs the energy of the antenna. Preliminary calculations of a design featuring a first conductive trace and a second conductive trace that at least partially encircled a sensor trace, unexpectedly showed that the gain (e.g. received power) of the antenna may be improved by more than 20% (1 dB) compared to a layout that does not include the additional metal traces. The described embodiments may save energy of the wireless link and provide a stable wireless data link or wireless power link between the eye-mountable device and an external device. In other embodiments, the sensor may be shielded by parallel traces or twisted traces.

FIG. 1 illustrates a functional block diagram of an ophthalmic device 100 with an antenna 140 and a sensor system 135 along with an external reader 105, in accordance with an embodiment of the disclosure. The exposed portion of ophthalmic device 100 includes an enclosure 110 formed to be contact-mounted to a corneal surface, sclera, or other portion of an eye a user. Alternatively, ophthalmic device 100 may be disposed within the eye of the user. Substrate 115 is embedded within or surrounded by enclosure 110 and provides a mounting surface for a power supply 120, a controller 125, an accommodation actuator 130, sensor system 135, antenna 140, and various interconnects 145 and 150. The illustrated embodiment of power supply 120 includes an energy harvesting antenna 155, charging circuitry 160, and a battery 165. The illustrated embodiment of controller 125 includes control logic 170, accommodation logic 175, and communication logic 180. The illustrated embodiment of reader 105 includes a processor 182, an antenna 184, and memory 186. The illustrated embodiment of memory 186 includes data storage 188 and program instructions 190.

Controller 125 is coupled to receive feedback control signals from sensor system 135 and further coupled to operate accommodation actuator 130. Power supply 120 supplies operating voltages to the controller 125 and/or the accommodation actuator 130. Antenna 140 is operated by the controller 125 to communicate information to and/or from eye-mountable device 100. In one embodiment, antenna 140, controller 125, power supply 120, and sensor system 135 are all situated on the embedded substrate 115. In one embodiment, accommodation actuator 130 is embedded within enclosure 110, but is not disposed on substrate 115. Because ophthalmic device 100 includes electronics and is configured to be contact-mounted to or disposed within an eye, it is also referred to herein as an ophthalmic electronics platform, eye-mountable device, contact lens, smart contact lens, or intraocular lens.

To facilitate contact-mounting, enclosure 110 may have a concave surface configured to adhere ("mount") to a moistened corneal surface (e.g., by capillary forces with a tear film coating the corneal surface). Additionally or alternatively, ophthalmic device 100 may be adhered by a vacuum force between the corneal surface and enclosure 110 due to the concave curvature. While mounted with the concave surface against the eye, the outward-facing surface of enclosure 110 may have a convex curvature that is formed to not interfere with eye-lid motion while ophthalmic device 100 is mounted to the eye. For example, enclosure 110 may be a substantially transparent curved disk shaped similarly to a contact lens.

Enclosure 110 may include one or more biocompatible materials, such as those employed for use in contact lenses or other ophthalmic applications. Enclosure 110 may optionally be formed in part from such biocompatible materials or may include an outer coating with such biocompatible materials. Enclosure 110 may include materials configured to moisturize the corneal surface, such as hydrogels and the like. In some instances, enclosure 110 may be a deformable ("non-rigid") material to enhance wearer comfort. In some instances, enclosure 110 may be shaped to provide a predetermined, vision-correcting optical power, such as can be provided by a contact lens. Enclosure 110 may be fabricated of various materials including a polymeric material, polyethylene terephthalate ("PET"), polymethyl methacrylate ("PMMA"), polyhydroxyethylmethacrylate ("polyHEMA"), a hydrogel, silicon based polymers (e.g., fluorosilicon acrylate) combinations of these, or otherwise.

Substrate 115 includes one or more surfaces suitable for mounting sensor system 135, controller 125, power supply 120, and antenna 140. Substrate 115 may be employed both as a mounting platform for chip-based circuitry (e.g., by flip-chip mounting) and/or as a platform for patterning conductive materials (e.g., gold, platinum, palladium, titanium, copper, aluminum, silver, nanowires, metals, other conductive materials, combinations of these, etc.) to create electrodes, interconnects, antenna(s), etc. In some embodiments, substantially transparent conductive materials (e.g., indium tin oxide or metal nanowire mesh) may be patterned on substrate 115 to form circuitry, electrodes, etc. For example, antenna 140 may be formed by depositing a pattern of gold or another conductive material on substrate 115. Similarly, interconnects 145 and 150 may be formed by depositing suitable patterns of conductive materials on substrate 115. A combination of resists, masks, and deposition techniques may be employed to pattern materials on substrate 115. Substrate 115 may be a relatively rigid material, such as polyethylene terephthalate ("PET"), Parylene C, Parylene HT, polyimide, liquid crystal polymer, or another material sufficient to structurally support the circuitry and/or electronics within enclosure 110. Ophthalmic device 100 may alternatively be arranged with a group of unconnected substrates rather than a single substrate. For example, controller 125 and power supply 120 may be mounted to one substrate, while antenna 140 and sensor system 135 are mounted to another substrate and the two may be electrically connected via interconnects.

In some embodiments, power supply 120, controller 125, and substrate 115 may be positioned away from the center of ophthalmic device 100 and thereby avoid interference with light transmission to the eye through the center of ophthalmic device 100. In contrast, accommodation actuator 130 may be centrally positioned to apply optical accommodation to the light transmitted to the eye through the center of ophthalmic device 100. For example, where ophthalmic device 100 is shaped as a concave-curved disk, substrate 115 may be embedded around the periphery (e.g., near the outer circumference) of the disk. In some embodiments, sensor system 135 includes a sensor trace electrically coupled to one or more discrete photodetectors (e.g. photodiodes), capacitors, electrochemical sensors, electrodes/traces, and the like, that are distributed, for example, to sense the eyelid overlap, gaze direction, analyte levels, and the like. Sensor system 135 and/or substrate 115 may be substantially transparent to incoming visible light to mitigate interference with light transmission to the eye.

Substrate 115 may be shaped as a flattened ring with a radial width dimension sufficient to provide a mounting platform for the embedded electronics components. Substrate 115 may have a thickness sufficiently small to allow the substrate to be embedded in enclosure 110 without adversely influencing the profile of eye-mountable device 100. Substrate 115 may have a thickness sufficiently large to provide structural stability suitable for supporting the electronics mounted thereon. For example, substrate 115 may be shaped as a ring with a diameter of about 10 millimeters, a radial width of about 1 millimeter (e.g., an outer radius 1 millimeter larger than an inner radius), and a thickness of about 50 micrometers. Substrate 115 may optionally be aligned with the curvature of the eye or of a surface of ophthalmic device 100 (e.g., convex surface). For example, substrate 115 may be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In the illustrated embodiment, power supply 120 includes a battery 165 to power the various embedded electronics, including controller 125. Battery 165 may be inductively charged by charging circuitry 160 and energy harvesting antenna 155. In some embodiments, battery 165 may be a capacitor. In one embodiment, antenna 140 and energy harvesting antenna 155 are independent antennae, which serve their respective functions of energy harvesting and communications. In another embodiment, energy harvesting antenna 155 and antenna 140 are the same physical antenna that provides respective functions for time-shared inductive charging and wireless communications with reader 105. Additionally or alternatively, power supply 120 may include a solar cell (i.e., photovoltaic cell) to capture energy from incoming ultraviolet, visible, and/or infrared radiation. Furthermore, an inertial power scavenging system may be included to capture energy from ambient vibrations.

Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) may be connected to function as a low-pass filter.

Controller 125 contains logic to choreograph the operation of the other embedded components. Control logic 170 controls the general operation of ophthalmic device 100, including providing a logical user interface, power control functionality, etc. Accommodation logic 175 includes logic for monitoring feedback signals from sensor system 135, determining the current gaze direction or focal distance of the user, and manipulating accommodation actuator 130 in response to provide the appropriate accommodation. The auto-accommodation may be implemented in real-time based upon feedback from the gaze tracking, or permit user control to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Ophthalmic device 100 may include various other embedded electronics and logic modules. For example, a light source or pixel array may be included to provide visible feedback to the user. An accelerometer or gyroscope may be included to provide positional, rotational, directional or acceleration feedback information to controller 125.

It is noted that the block diagram shown in FIG. 1 is described in connection with functional modules for convenience in description, but does not necessarily connote physical organization. Rather, embodiments of ophthalmic device 100 may be arranged with one or more of the functional modules ("sub-systems") implemented in a single chip, multiple chips, in one or more integrated circuits, or otherwise.

External reader 105 includes an antenna 184 (or group of more than one antennas) to send and receive wireless signals 171 to and from ophthalmic device 100. External reader 105 also includes a computing system with a processor 182 in communication with a memory 186. Memory 186 is a non-transitory computer-readable medium that may include, without limitation, magnetic disks, optical disks, organic memory, and/or any other volatile (e.g. RAM) or non-volatile (e.g. ROM) storage system readable by the processor 182. Memory 186 may include a data storage 188 to store indications of data, such as data logs (e.g., user logs), program settings (e.g., to adjust behavior of ophthalmic device 100 and/or external reader 105), etc. Memory 186 may also include program instructions 190 for execution by processor 182 to cause the external reader 105 to perform processes specified by the instructions 190. For example, program instructions 190 may cause external reader 105 to provide a user interface that allows for retrieving information communicated from ophthalmic device 100 or allows transmitting information to ophthalmic device 100 to program or otherwise select operational modes of ophthalmic device 100. External reader 105 may also include one or more hardware components for operating antenna 184 to send and receive wireless signals 171 to and from ophthalmic device 100.

External reader 105 may be a smart phone, digital assistant, or other portable computing device with wireless connectivity sufficient to provide the wireless communication link 171. Wireless communication link 171 may a wireless power link, a wireless data link, or a combination thereof. External reader 105 may also be implemented as an antenna module that can be plugged in to a portable computing device, such as in an example where the communication link 171 operates at carrier frequencies not commonly employed in portable computing devices. In some instances, external reader 105 is a special-purpose device configured to be worn relatively near a wearer's eye to allow the wireless communication link 171 to operate with a low power budget. For example, the external reader 105 may be integrated in a piece of jewelry such as a necklace, earing, etc. or integrated in an article of clothing worn near the head, such as a hat, headband, etc.

Figure 2A:
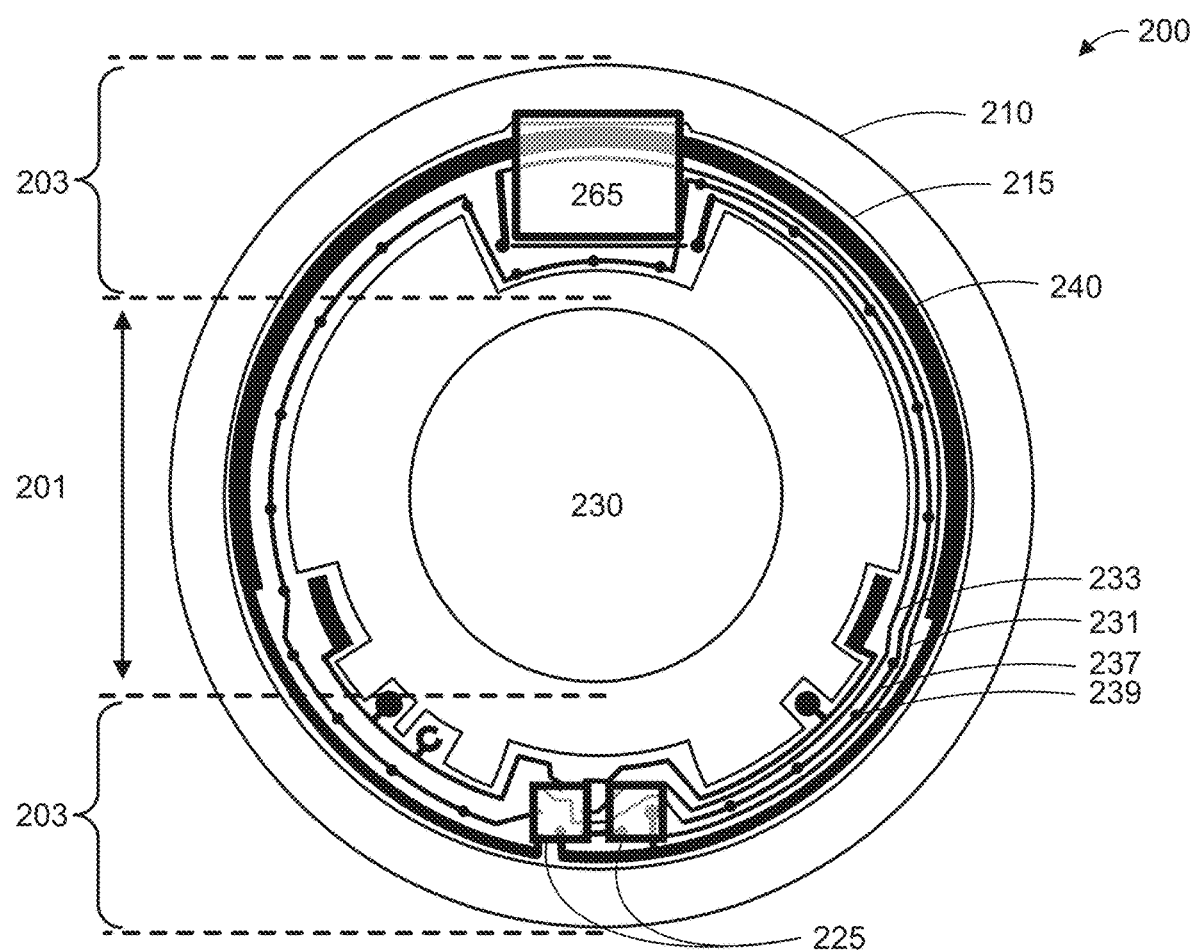
FIG. 2A illustrates a top view of an eye-mountable device, in accordance with an embodiment of the disclosure.
Figure 2B:
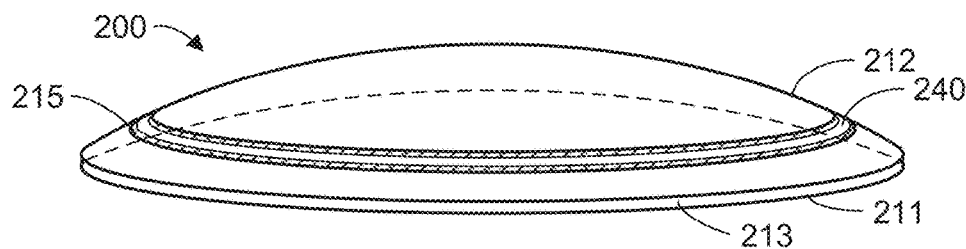
FIG. 2B illustrates a perspective view of an eye-mountable device, in accordance with an embodiment of the disclosure.

FIGS. 2A and 2B illustrate two views of eye-mountable device 200, in accordance with an embodiment of the disclosure. FIG. 2A is a top view of eye-mountable device 200 while FIG. 2B is a perspective view of the same. Eye-mountable device 200 is one possible implementation of ophthalmic device 100 illustrated in FIG. 1. The illustrated embodiment of eye-mountable device 200 includes enclosure 210, substrate 215, battery 265, controller 225, accommodation actuator 230, first conductive trace 231, second conductive trace 233, sensor trace 237, sensors 239, and antenna 240. First conductive trace 231, second conductive trace 233, sensor trace 237, and sensors 239 may be part of a sensor system (e.g. sensor system 135 illustrated in FIG. 1). It should be noted that while discrete sensors such as sensors 239 are illustrated, it is appreciated that sensor trace 237 itself may be a sensor and thus in some embodiments sensors 239 may not be included. In one embodiment, sensor trace 237 is configured as a single loop inductor that resonates with a capacitor included in controller 225. It should also be appreciated that FIGS. 2A and 2B are not necessarily drawn to scale, but have been illustrated for purposes of explanation only in describing the arrangement of the example eye-mountable device 200.

Enclosure 210 of eye-mountable device 200 is shaped as a curved disk that includes a central region 201 surrounded by a peripheral region 203. In the illustrated embodiment, accommodation actuator 230 is disposed, at least partially, within central region 201, which is surrounded peripheral region 203. Peripheral region 203 may encompass the area between an outer edge 213 of the enclosure and central region 201. Enclosure 210 includes one or more substantially transparent material to allow incident light to be transmitted to the eye while eye-mountable device 200 is mounted to the eye. Enclosure 210 may be formed with one side having a concave surface 211 suitable to fit over a corneal or other surface of an eye. The opposite side of the disk may have a convex surface 212 that does not interfere with eyelid motion while eye-mountable device 200 is mounted to the eye. In the illustrated embodiment, a circular or oval outer edge 213 connects the concave surface 211 and convex surface 212.

As illustrated, controller 225, first conductive trace 231, second conductive trace 233, sensor trace 237, antenna 240, and battery 265 are disposed in peripheral region 203 of eye-mountable device 200 that surrounds central region 201. Antenna 240 is disposed between outer edge 213 and central region 201 of eye-mountable device 200. Sensor trace 237 is disposed between antenna 240 and central region 201. First conductive trace 231 is at least partially disposed between at least one of antenna 240 and sensor trace 237 or central region 201 and sensor trace 237. Battery 265 is mounted to substrate 215 and partially overlaps first conductive trace 231, sensor trace 237, and antenna 240. However, in other embodiments, battery 265 may be disposed within peripheral region 203 of eye-mountable device 200 between antenna 240 and central region 201. An advantage of battery 265 being disposed between antenna 240 and central region 201 such that battery 265 does not overlap antenna 240 is a potential reduction in electromagnetic coupling between battery 265 and antenna 240 which may result in an increased gain for antenna 240. Accommodation actuator 230 may include an electro-active accommodating optic at least partially surrounded by first conductive trace 231 and second conductive trace 233. The electro-active accommodating optic may be a liquid crystal optic, an electrowetting optic, or any other electro-active adjustable optic to adjust an index of refraction of light at the central region 201 to provide vision accommodation to a wearer of eye-mountable device 200.

Eye-mountable device 200 may have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of eye-mountable device 200 may be selected according to the size and/or shape of the corneal surface of the wearer's eye. Enclosure 210 may be formed with a curved shape in a variety of ways. For example, techniques similar to those employed to form vision-correction contact lenses, such as heat molding, injection molding, spin casting, etc. can be employed to form enclosure 210.

Substrate 215 is embedded within enclosure 210. Substrate 215 may be embedded within peripheral region 203 of eye-mountable device 200, which is away from central region 201 where accommodation actuator 230 is positioned. Substrate 215 does not interfere with vision because it is too close to the eye to be in focus and is positioned away from central region 201 where incident light is transmitted to the light-sensing portions of the eye. In some embodiments, substrate 215 may optionally be formed of a transparent material to further mitigate effects on visual perception. Substrate 215 may be shaped as a flat, circular ring (e.g., a disk with a centered hole, an annulus) that encircles accommodation actuator 230. The flat surface of substrate 215 (e.g., along the radial width) is a platform for mounting electronics and for patterning conductive materials to form electrodes, traces, antenna(s), and/or interconnections. In some embodiments, some or all of controller 225, battery 265, first conductive trace 231, second conductive trace 233, sensor trace 237, sensors 239, and antenna 240 may be mounted to substrate 215 to share a common plane.

Controller 225 contains logic to choreograph the operation of the other embedded components. Controller 225 may be implemented with a single chip, or as illustrated with multiple chips. Controller 225 is mounted to substrate 215 at approximately the 6 o'clock position, but it is appreciated that controller 225 may be mounted to any position and on either side of substrate 215. Similarly, battery 265 is mounted to substrate 215 at the 12 o'clock position, but may also be positioned elsewhere. Controller 225 is coupled to battery 265 via the first conductive trace 231 and the second conductive trace 233. In one embodiment, first conductive trace 231 is coupled or otherwise connected to a positive terminal of battery 265, while second conductive trace 233 is coupled or otherwise connected to a reference terminal (e.g., a ground terminal or a negative terminal) of battery 265. Conversely, in another embodiment, first conductive trace 231 is coupled or otherwise connected to a reference terminal (e.g., a ground terminal or a negative terminal) of battery 265, while second conductive trace 233 is coupled or otherwise connected to a positive terminal of battery 265. Moreover, battery 265 provides power (e.g., via a supply voltage, current, or the like) to controller 225 via first conductive trace 231 and second conductive trace 233. However, it is appreciated in other embodiments, first conductive trace 231 and second conductive trace 233 may be coupled to other electrical components, left floating, coupled to one another, or otherwise. Antenna 240 is also coupled to controller 225 to provide at least one of wireless communication for eye-mountable device 200 or inductive charging of battery 265.

Eye-mountable device 200 includes a sensor system that is one possible implementation of the sensor system 135 of FIG. 1. In one embodiment, the sensor system of eye-mountable device 200 includes sensor trace 237 which is electrically coupled to one or more discrete sensors 239 such as photodetectors (e.g. photodiodes), capacitors, electrochemical sensors, electrodes/traces, and the like. In some embodiments, sensors 239 are distributed to generate measurements to sense the eyelid overlap, determine a gaze direction of the eye of the user, analyte levels of the user, and the like. In the illustrated embodiment, sensors 239 are disposed along sensor trace 237, but such positioning should not be deemed limiting as sensors 239 may be positioned anywhere within enclosure 210. Rather, the positioning of sensors 239 may be determined by the design engineer based on the measurement to be obtained. In other embodiments, sensor trace 237 is itself the sensor and thus sensors 239 may not necessarily be needed or included within eye-mountable device 200. Sensor trace 237 may be a single loop inductor that resonates with a capacitor included in controller 225.

Figure 3A:
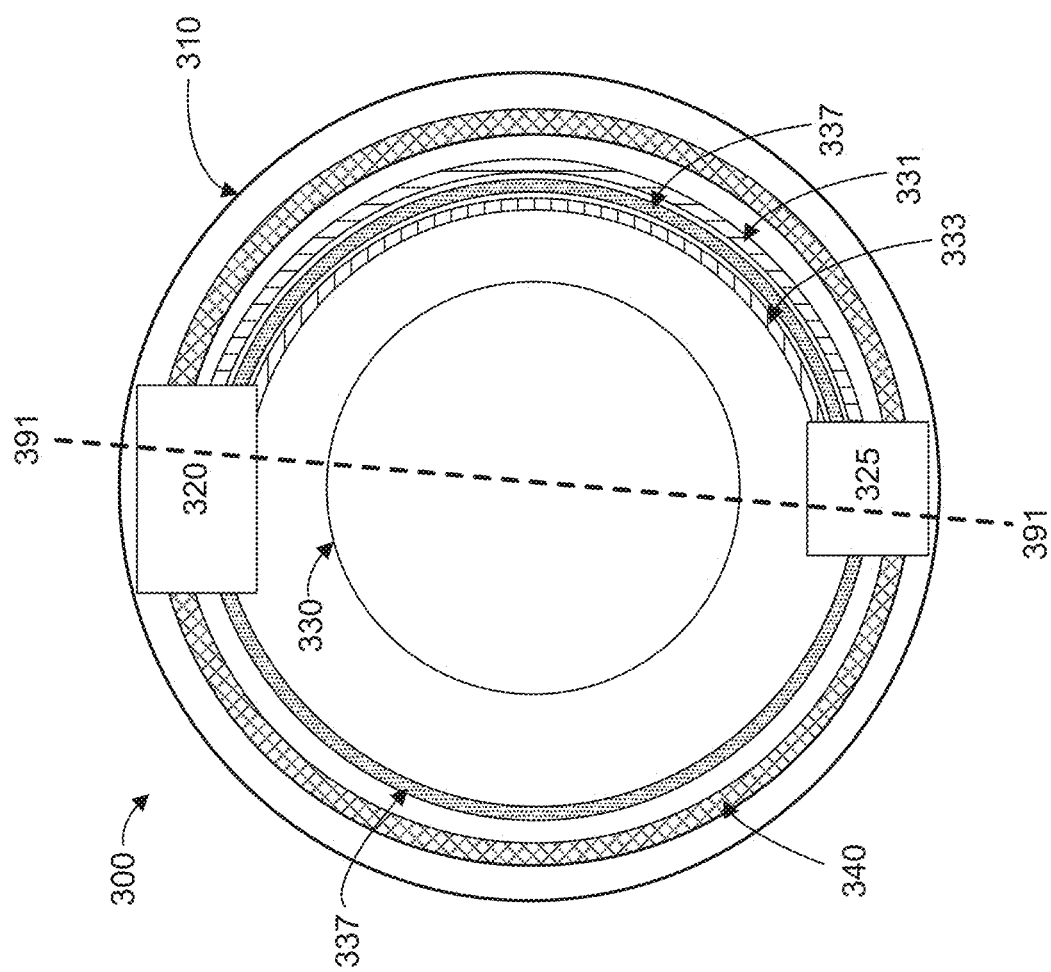
FIGS. 3A-3C illustrate a top view of an eye-mountable device with different component layouts, each in accordance with a corresponding embodiment of the disclosure.
Figure 3B:
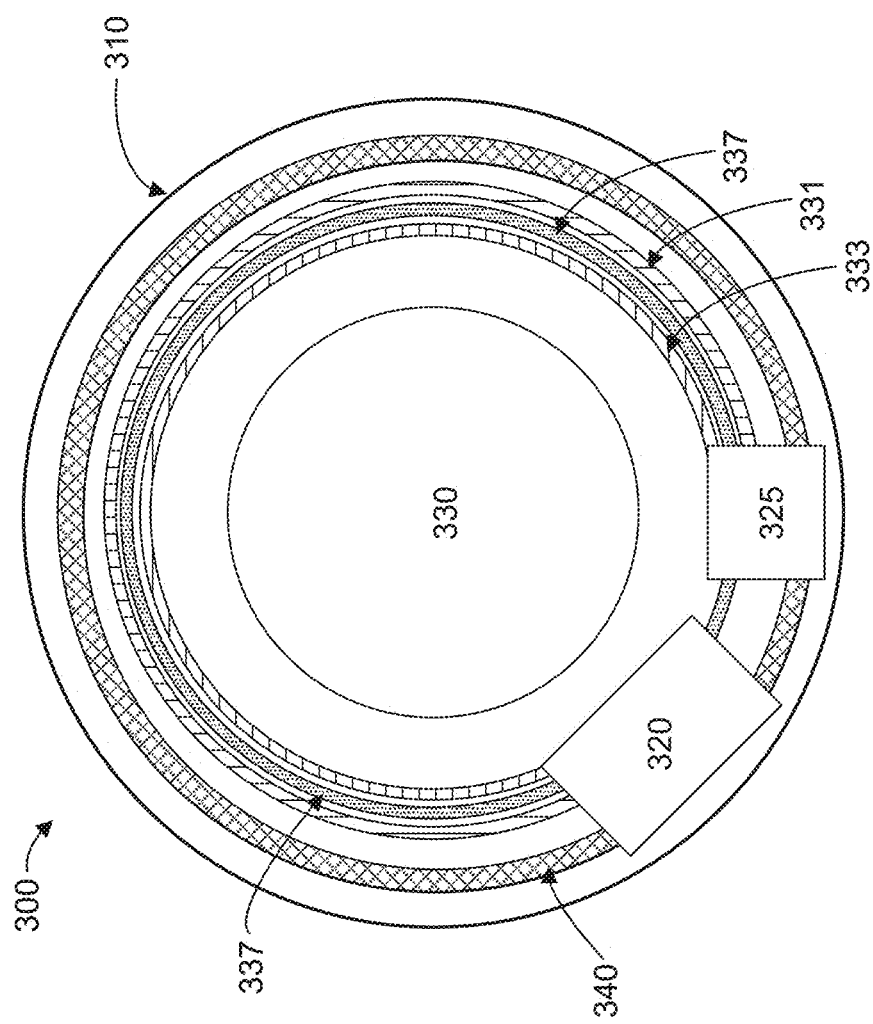
Figure 3C:
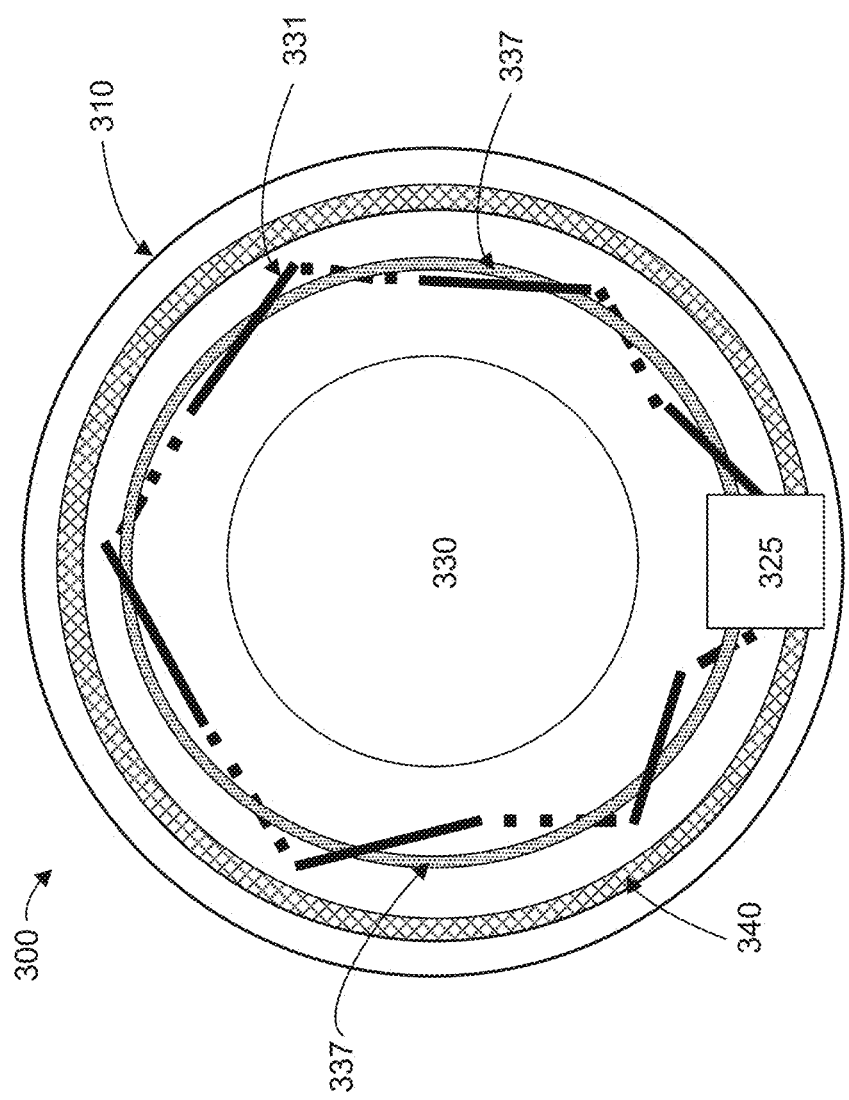

FIGS. 3A-3C illustrate a top view of an eye-mountable device 300 with different component layouts, each in accordance with a corresponding embodiment of the disclosure. Eye-mountable device 300 is one possible implementation of ophthalmic device 100 illustrated in FIG. 1 and/or ophthalmic device 200 illustrated in FIG. 2A. As illustrated in FIGS. 3A-3C, eye-mountable device 300 may include an enclosure 310 and a central region 330 surrounded by a peripheral region. The peripheral region may be the area between an outer edge of eye-mountable device 300 and central region 330. Disposed within the peripheral region of eye-mountable device 300 is a first electronic component 325 (e.g., controller 125 illustrated in FIG. 1 and/or controller 225 illustrated in FIG. 2A) at a first position, a second electronic component 320 (e.g., battery 165 illustrated in FIG. 1 and/or battery 265 illustrated in FIG. 2A) at a second position, a first conductive trace 331 (e.g., first conductive trace 231 of FIG. 2A), a second conductive trace 333 (e.g., second conductive trace 233 of FIG. 2A), a sensor trace 337 (e.g., sensor trace 237 of FIG. 2A), and an antenna 340 (e.g., antenna 140 of FIG. 1 and/or antenna 240 of FIG. 2A). Antenna 340 at least partially encircles sensor trace 337 by extending within the peripheral region proximate to an outer edge of eye-mountable device 300.

FIG. 3A illustrates a top view of a component layout of eye-mountable device 300, in accordance with an embodiment of the disclosure. In the illustrated embodiment, first conductive trace 331 and second conductive trace 333 each extend alongside opposite sides of sensor trace 337 to at least partially surround a segment of sensor trace 337. More specifically, first conductive trace 331 and second conductive trace 333 are configured to couple first electronic component 325 to second electronic component 320. The segment of sensor trace 337 is disposed between first electronic component 325 and second electronic component 320. First conductive trace 331 and second conductive trace 333 are positioned proximate to sensor trace 337 to inhibit electromagnetic coupling between antenna 340 and sensor trace 337. This may be achieved, in part, by positioning second conductive trace 333 between central region 330 and sensor trace 337 and first conductive trace 331 between antenna 340 and sensor trace 337. In the same or other embodiments, first conductive trace 331 and second conductive trace 333 extend substantially parallel to the segment of sensor trace 337.

The amount or effectiveness of shielding between sensor trace 337 and antenna 340 may be determined, in part, by the extent that first conductive trace 331 and second conductive trace 333 surround or otherwise encircle sensor trace 337. In one embodiment, first conductive trace 331 and second conductive trace 333 may be capacitively or inductively coupled to sensor trace 337 such that they may interfere with the measurement of the sensor system (e.g. cross talk, diminished signal to noise ratio, etc.). Conversely, if first conductive trace 331 and second conductive trace 333 do not surround sensor trace 337 to enough of an extent, the coupling between sensor trace 337 and antenna 340 may result in an unstable wireless connection provided by antenna 340. Consequently, design engineers must carefully balance the design of eye-mountable device 300 to meet the desired device requirements.

In the illustrated embodiment, first electronic component 325 is coupled to second electronic component 320 via first conductive trace 331 and second conductive trace 333. In other words, design engineers may adjust the first position of first electronic component 325 and the second position of second electronic component 320 to control the extent by which first conductive trace 331 and second conductive trace 333 surround sensor trace 337. As illustrated, central region 330 is disposed between the first position and the second position such that first electronic component 325 and second electronic component 320 are positioned along a common diameter line 391 along a diameter of eye-mountable device 300. Thus, first conductive trace 331 and second conductive trace 333 extend halfway or less around central region 330.

Alternatively, in the embodiment illustrated in FIG. 3B, first conductive trace 331 and second conductive trace 333 may extend more than halfway around the central region. This may be achieved by having the first position and the second position disposed within a first quadrant of eye-mountable device 300. Accordingly, first conductive trace 331 and second conductive trace 333 may almost completely surround central region 330. In some embodiments, the optimal layout of first conductive trace 331, second conductive trace 333, sensor trace 337, and antenna 340 may be based on a balanced weight distribution on eye-mountable device 300.

In the same or other embodiments, the first position and the second position are arranged symmetrically within the peripheral region of enclosure 310 to provide an even weight distribution of first electronic component 325 and second electronic component 320. An advantage of the even weight distribution is that eye-mountable device 300 may remain fixed in position while mounted to the eye of the user.

In one embodiment, first electronic component 325 is a controller, second electronic component 320 is power supply (e.g. a battery with associated circuitry such as control circuitry), and sensor trace 337 is included in a sensor system as described in accordance with embodiments of the disclosure. Controller 325 may include logic and or instructions that when executed by the controller causes the eye-mountable device 300 to perform operations including determining a gaze direction of the eye of the user based on measurements from the sensor system. The battery may provide the power necessary for controller 325 to perform the measurements.

FIG. 3C illustrates a top view of another component layout of eye-mountable device 300, in accordance with an embodiment of the disclosure. Eye-mountable device 300 illustrated in FIG. 3C is similar to that of the embodiments illustrated in FIG. 3A and FIG. 3B, and is one possible implementation of ophthalmic device 100 illustrated in FIG. 1.

One difference, is that eye-mountable device 300 of FIG. 3C illustrates an alternative way to inhibit electromagnetic coupling between sensor trace 337 and antenna 340 with just first conductive trace 331. First conductive trace 331 repeatedly coils around sensor trace 337 to inhibit electromagnetic coupling between antenna 340 and the sensor system. As illustrated, eye-mountable device 300 includes a first electronic component 325 having a first side and a second side opposite the first side. First conductive trace 331, sensor trace 337, and antenna 340 each extend from the first side of the first electronic component to the second side of the first electronic component to fully surround central region 330.

Figure 4:
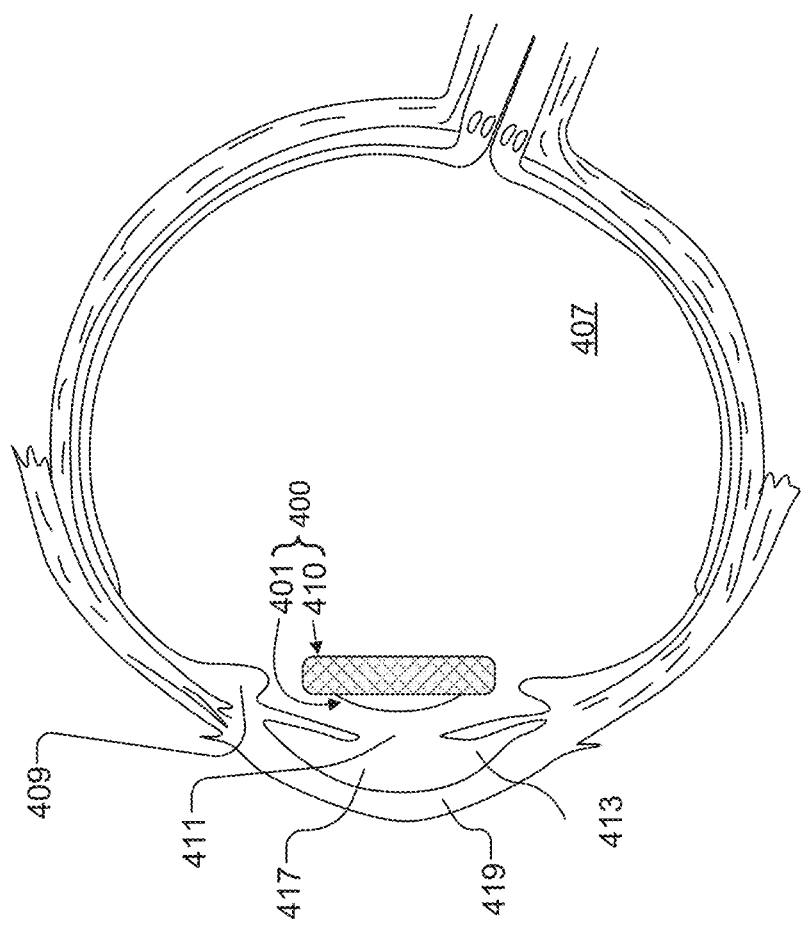
FIG. 4 illustrates a perspective view of an intraocular device implanted in a user's eye, in accordance with an embodiment of the disclosure.

FIG. 4 illustrates a perspective view of an intraocular device 400 implanted in a user's eye 407, in accordance with an embodiment of the disclosure. Intraocular device 400 is one possible implementation of ophthalmic device 100 illustrated in FIG. 1. As illustrated, intraocular device 400 is positioned where the natural eye lens would typically be located proximate to ciliary muscle 409. In particular, intraocular device 400 is implanted within the posterior chamber 411 behind an iris 413 of eye 407. However, intraocular device 400 may be implanted into other locations, as well, such as anterior chamber 417 disposed between iris 413 and cornea 419.

The illustrated embodiment of intraocular device 400 includes a lens 401 hermetically sealed within enclosure 410. In one embodiment, lens 401 is an extension of enclosure 410. Enclosure 410 may have a concave surface to shape or otherwise adjust incoming light towards eye 407. Intraocular device 400 may include the same or similar features, structures, characteristics, or combination therefore in accordance with embodiments of the disclosure.

The processes explained above are described in terms of computer software and hardware. The techniques described may constitute machine-executable instructions embodied within a tangible or non-transitory machine (e.g., computer) readable storage medium, that when executed by a machine (e.g., controller 125) will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device, comprising:
an enclosure configured to mount on or in an eye of a user;
a central region surrounded by a peripheral region;
an antenna disposed within the peripheral region, wherein the antenna is disposed between an outer edge of the ophthalmic device and the central region;
a sensor system including a sensor trace disposed within the peripheral region between the antenna and the central region; and
a first conductive trace and a second conductive trace, wherein the first conductive trace is at least partially disposed between the antenna and the sensor trace, and wherein the first conductive trace and the second conductive trace each extend along opposite sides of the sensor trace to inhibit electromagnetic coupling between the antenna and the sensor system.

2. The ophthalmic device of claim 1, wherein the second conductive trace is disposed between the central region and the sensor trace.

3. The ophthalmic device of claim 1, further comprising:
a first electronic component disposed within the peripheral region at a first position; and
a second electronic component coupled to the first electronic component via the first conductive trace and the second conductive trace, wherein the second electronic component is disposed within the peripheral region at a second position.

4. The ophthalmic device of claim 3, wherein the central region is disposed between the first position and the second position such that the first electronic component and the second electronic component are positioned along a common diameter line of the ophthalmic device, and wherein the first conductive trace and the second conductive trace extend up to half way around the central region.

5. The ophthalmic device of claim 3, wherein the first position and the second position are disposed within a first quadrant of the ophthalmic device, wherein the first conductive trace and the second conductive trace extend more than half way around the central region.

6. The ophthalmic device of claim 3, wherein the first position and the second position are arranged symmetrically within the peripheral region to provide an even weight distribution of the first electronic component and the second electronic component.

7. The ophthalmic device of claim 3, wherein the first electronic component is a controller including logic that when executed performs operations including:
determining a gaze direction of the eye of the user based on measurements from the sensor system, and wherein the second electronic component is a battery to provide power to the controller.

8. The ophthalmic device of claim 7, wherein the sensor system includes sensors disposed along and electrically coupled to the sensor trace, wherein the sensors include at least one of a capacitive type position sensor, an inductive type position sensor, or a photodetector to generate the measurements.

9. The ophthalmic device of claim 7, wherein the sensor trace is a position sensor that is coupled to the controller.

10. The ophthalmic device of claim 9, wherein the sensor trace is configured as a single loop inductor that resonates with a capacitor included in the controller for position sensing.

11. The ophthalmic device of claim 7, wherein the battery is disposed in the peripheral region between the antenna and the central region.

12. The ophthalmic device of claim 7, wherein the antenna is coupled to the controller to provide at least one of wireless communication for the ophthalmic device or inductive charging of the battery.

13. The ophthalmic device of claim 1, further comprising a first electronic component having a first side and a second side opposite the first side, wherein the first electronic component is disposed within the peripheral region, and wherein the antenna, the sensor trace, and the first conductive trace extend from the first side of the first electronic component within the peripheral region to the second side of the first electronic component to surround the central region.

14. The ophthalmic device of claim 1, further comprising:
a substrate disposed within the peripheral region, wherein the antenna, the sensor trace, and the first conductive trace are disposed on the substrate to share a common plane.

15. A system for a smart contact lens, the system comprising:
a central region surrounded by a peripheral region;
an antenna disposed within the peripheral region proximate to an outer edge of the smart contact lens;
a sensor trace disposed within the peripheral region, wherein the sensor trace is at least partially encircled by the antenna; and
a first conductive trace and a second conductive trace that each extend along opposite sides of the sensor trace to inhibit electromagnetic coupling between the antenna and the sensor trace, wherein the second conductive trace is disposed between the central region and the sensor trace, and wherein the first conductive trace is disposed between the sensor trace and the antenna.

16. The system of claim 15, wherein the first conductive trace and the second conductive trace are disposed within the peripheral region and extend substantially parallel to a first segment of the sensor trace.

17. The system of claim 15, further comprising:
a first electronic component disposed within the peripheral region at a first position; and
a second electronic component coupled to the first electronic component via the first conductive trace and the second conductive trace, wherein the second electronic component is disposed within the peripheral region at a second position.

18. The system of claim 17, wherein the central region is disposed between the first position and the second position such that the first electronic component and the second electronic component are positioned along a common diameter line of the smart contact lens, and wherein the first conductive trace and the second conductive trace extend approximately half way around the central region.

19. The system of claim 15, further comprising an accommodation actuator disposed within the central region, wherein the accommodation actuator includes a liquid crystal material at least partially surrounded by the first conductive trace and the second conductive trace.

20. An ophthalmic device, comprising:
an enclosure configured to mount on or in an eye of a user;
a central region surrounded by a peripheral region;
an antenna disposed within the peripheral region, wherein the antenna is disposed between an outer edge of the ophthalmic device and the central region;
a sensor system including a sensor trace disposed within the peripheral region between the antenna and the central region; and
a first conductive trace positioned to repeatedly coil around the sensor trace to inhibit electromagnetic coupling between the antenna and the sensor system.

21. An ophthalmic device, comprising:
an enclosure configured to mount on or in an eye of a user;
a central region surrounded by a peripheral region;
an antenna disposed within the peripheral region, wherein the antenna is disposed between an outer edge of the ophthalmic device and the central region;
a sensor system including a sensor trace disposed within the peripheral region between the antenna and the central region;
a first conductive trace and a second conductive trace extending along opposite sides of the sensor trace, wherein the first conductive trace is disposed between the antenna and the sensor trace;
a first electronic component disposed within the peripheral region at a first position; and
a second electronic component coupled to the first electronic component via the first conductive trace and the second conductive trace, wherein the second electronic component is disposed within the peripheral region at a second position,
wherein the central region is disposed between the first position and the second position such that the first electronic component and the second electronic component are positioned along a common diameter line of the ophthalmic device, and wherein the first conductive trace and the second conductive trace extend up to half way around the central region.

* * * * *